United States Patent
Xu et al.

(10) Patent No.: US 12,315,046 B2
(45) Date of Patent: May 27, 2025

(54) LOW RADIATION DOSE COMPUTED TOMOGRAPHY PERFUSION (CTP) WITH IMPROVED QUANTITATIVE ANALYSIS

(71) Applicant: KONINKLIJKE PHILIPS N.V., Eindhoven (NL)

(72) Inventors: Shiyu Xu, Mayfield Heights, OH (US); Hao Dang, Mayfield Heights, OH (US); Chuanyong Bai, Solon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1320 days.

(21) Appl. No.: 16/965,949

(22) PCT Filed: Jan. 30, 2019

(86) PCT No.: PCT/EP2019/052168
§ 371 (c)(1),
(2) Date: Jul. 29, 2020

(87) PCT Pub. No.: WO2019/149718
PCT Pub. Date: Aug. 8, 2019

(65) Prior Publication Data
US 2021/0085273 A1 Mar. 25, 2021

Related U.S. Application Data

(60) Provisional application No. 62/624,871, filed on Feb. 1, 2018.

(51) Int. Cl.
*G06K 9/00* (2022.01)
*A61B 6/00* (2006.01)
(Continued)

(52) U.S. Cl.
CPC ............ *G06T 11/008* (2013.01); *A61B 6/032* (2013.01); *A61B 6/481* (2013.01); *A61B 6/52* (2013.01);
(Continued)

(58) Field of Classification Search
CPC . G06T 2207/10081; G06T 2207/20084; G06T 11/003; A61B 6/032
See application file for complete search history.

(56) References Cited

U.S. PATENT DOCUMENTS 7,496,175 B2 2/2009 Sakaguchi
2007/0092055 A1 4/2007 Vives
(Continued)

FOREIGN PATENT DOCUMENTS

JP 2014144372 A 8/2014
WO WO2017192629 A1 11/2017

OTHER PUBLICATIONS

Long, Gucan, et al. "Learning image matching by simply watching video." Computer Vision—ECCV 2016: 14th European Conference, Amsterdam, The Netherlands, Oct. 11-14, 2016, Proceedings, Part VI 14. Springer International Publishing, 2016. (Year: 2016).*
(Continued)

*Primary Examiner* — Gregory A Morse
*Assistant Examiner* — Owais Iqbal Memon
(74) *Attorney, Agent, or Firm* — Larry Liberchuk

(57) ABSTRACT

A computer tomography scanner (102) includes a radiation source (112) configured to emit x-ray radiation, a detector array (116) configured to detect x-ray radiation and generate a signal indicative thereof, and a reconstructor (118) configured to reconstruct the signal and generate sequential spares time line perfusion volumetric image data. The computer tomography scanner further includes a processor (132) configured to process the sequential spares time line perfu- (Continued)

sion volumetric image data using a trained neural network of a perfusion data enhancing module (136) to produce sequential dense time line perfusion volumetric image data.

14 Claims, 5 Drawing Sheets

(51) Int. Cl.
*A61B 6/03* (2006.01)
*G06T 11/00* (2006.01)

(52) U.S. Cl.
CPC ..... *G06T 2210/41* (2013.01); *G06T 2211/441* (2023.08); *G06T 2211/444* (2023.08)

(56) References Cited

U.S. PATENT DOCUMENTS

| | | | |
|---|---|---|---|
| 2012/0141005 | A1 | 6/2012 | Djeridane |
| 2014/0257094 | A1 | 9/2014 | Meetz |
| 2016/0073992 | A1 | 3/2016 | Liu |
| 2016/0292382 | A1* | 10/2016 | Grady ............... A61B 5/02007 |
| 2017/0007195 | A1 | 1/2017 | Molloi |
| 2019/0150764 | A1* | 5/2019 | Arnold .................. G06V 10/82 |
| 2019/0236818 | A1* | 8/2019 | Ritter ................... G06T 11/008 |

OTHER PUBLICATIONS

PCT International Search Report, International application No. PCT/EP2019/052168, Mar. 18, 2019.

Neukirchen C. et al., "An Iterative Method for Tomographic X-Ray Perfusion Estimation in a Decomposition Model-Based Approach", Medical Physics, AIP, Melville, NY, vol. 37, No. 12, Nov. 8, 2010.

Andreas F. et al., "Interventional 4-D C-Arm CT Perfusion Imaging Using Interleaved Scanning and Partial Reconstruction Interpolation", IEEE Transactions on Medical Imaging., vol. 31, No. 4, Apr. 1, 2012.

Chen H. et al., "Low-Dose CT Via Deep Neural Network", Biomedical Optics Express, vol. 8, Issue 2, pp. 679-694, 2017.

Gouk H.G.R. et al., "Fast Sliding Window Classification with Convolutional Neural Networks," IVNVZ '14 Proceedings of the 29th International Conference on Image and Vision Computing New Zealand, pp. 114-118, Nov. 19-21, 2014.

Long J. et al., "Fully Convolutional Networks for Semantic Segmentation." Proceedings of the IEEE Conference on Computer Vision and Pattern Recognition (CVPR), 2015, pp. 3431-3440.

Ronneberger O. et al., "U-Net: Convolutional Networks for Biomedical Image Segmentation", Medical Image Computing and Computer-Assisted Intervention (MICCAI), Springer, LNCS, vol. 9351: 234-241, 2015.

* cited by examiner

LOW RADIATION DOSE COMPUTED TOMOGRAPHY PERFUSION (CTP) WITH IMPROVED QUANTITATIVE ANALYSIS

FIELD OF THE INVENTION

The following generally relates to imaging and more particularly to low radiation dose computed tomography perfusion (CTP) with improved quantitative analysis.

BACKGROUND OF THE INVENTION

Computed tomography perfusion (CTP) imaging is an imaging technique which captures the transit of an administered contrast (e.g., iodine) agent through vascular tissue of interest such as a vessel and/or an organ. Generally, for CTP imaging, a contrast agent bolus is administered to a patient, and the region of interest of the patient including the vascular tissue of interest is scanned. The contrast agent causes the x-ray density in the vascular tissue of interest to temporarily increase as the contrast agent flows through the vascular tissue. A typical perfusion scan includes acquiring data of the same region, over multiple time intervals, covering, e.g., contrast agent arrival, uptake and wash out.

Analysis of the acquired data can be used to determine a perfusion state of the vascular tissue of interest, e.g., based on the contrast agent dynamics. For cardiac applications, this may include quantifying the contrast agent distribution in the cardiac muscle over time. Such analysis may include determining various perfusion related information for the vascular tissue of interest such as a time-attenuation curve, blood flow, blood volume, mean transit time, maximum upslope, time to peak, etc. This information can be used to identify ischemic tissue and/or differentiate between irreversibly damaged (or necrotic) tissue and potentially reversibly damaged (or at-risk) tissue.

However, x-ray radiation is ionizing radiation, which can kill or damage cells and/or increase risk of cancer. With CTP imaging, x-rays have been turned on continuously for thirty or more seconds, which is considered high patient x-ray dose. One approach to reduce x-ray dose is to perform sparse scans in the temporal domain where the patient is not continuously scanned. Unfortunately, a larger time interval between scans can degrade the accuracy of quantitative measurements. Another approach includes performing advanced iterative reconstruction (IR). However, IR requires intensive computation and increases the time of the overall reconstruction. Furthermore, reducing x-ray dose increases noise, which degrades image quality.

SUMMARY OF THE INVENTION

Aspects described herein address the above-referenced problems and others.

In one aspect, a computer tomography scanner includes a radiation source configured to emit x-ray radiation, a detector array configured to detect x-ray radiation and generate a signal indicative thereof, and a reconstructor configured to reconstruct the signal and generate sequential sparse time line perfusion volumetric image data. The computer tomography scanner further includes a processor configured to process the sequential sparse time line perfusion volumetric image data using a trained neural network of a perfusion data enhancing module to produce sequential dense time line perfusion volumetric image data.

In another aspect, a computer tomography scanner includes a radiation source configured to emit x-ray radiation, a detector array configured to detect x-ray radiation and generate a signal indicative thereof, and a reconstructor configured to reconstruct the signal and generate sequential sparse time line perfusion volumetric image data. The computer tomography scanner further includes a processor configured to train a neural network to predict sequential dense time line perfusion volumetric image data from training sequential sparse time line perfusion volumetric image data and training sequential dense time line perfusion volumetric image data.

In another aspect, a computer readable storage medium is encoded with computer readable instructions, which, when executed by a computer processor of a computing system, causes the computer processor to: process sequential sparse time line perfusion volumetric image data using a trained neural network to produce sequential dense time line perfusion volumetric image data.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following describes an approach for low radiation dose CTP with improved quantitative analysis. CTP imaging is considered a high x-ray dose procedure. The x-ray dose can be decreased, e.g., by performing a sparse scan in the temporal domain in which x-rays are not continuously on. However, this decrease temporal resolution and hence the accuracy of quantitative measurements. A linear interpolation can generate time dense images from time sparse images. However, the contrast agent does not flow in vessels at a constant speed and, thus, the distribution of contrast agent may not be linear to time. As a consequence, the linear interpolated images tend to be arbitrary and lose information.

In an embodiment described herein, a neural network is trained to learn the structure of vessel/tissue, the spatially intensity distribution in vessel/tissue, and how contrast agent flows in vessels/tissues with different structure and different intensity distribution. The trained neural network can then process a set of sparse time line CTP images and produce a set of dense time line CTP images with increased temporal resolution and hence accuracy of quantitative measurements.

Figure 1:
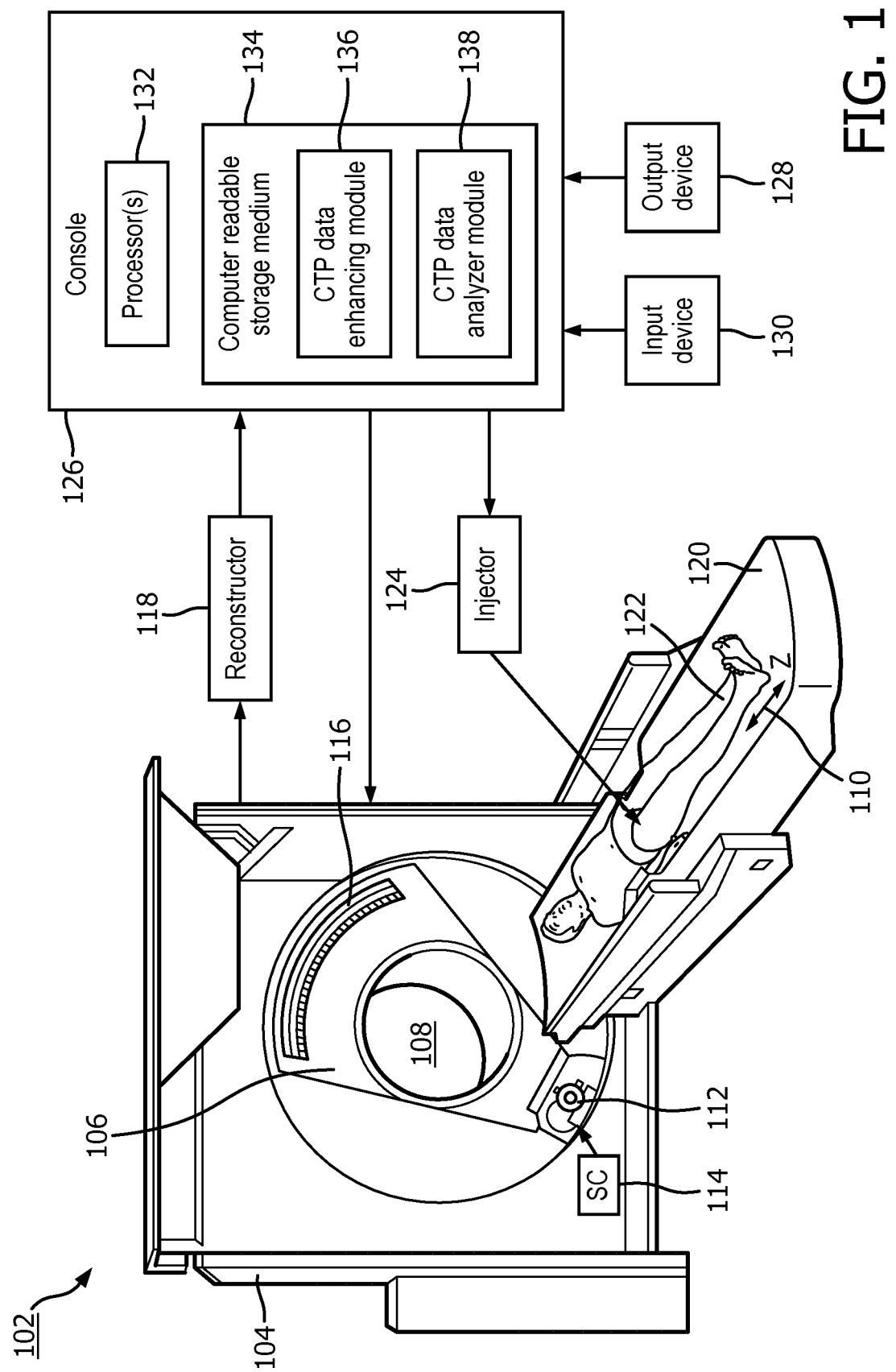
FIG. 1 schematically illustrates an example CT scanner including a CTP data enhancing module with a neural network for predicting sequential dense time line CTP volumetric image data from sequential sparse time line CTP volumetric image data.

FIG. 1 schematically illustrates an example computed tomography (CT) scanner 102. The CT scanner 102 includes a stationary gantry 104 and a rotating gantry 106, which is rotatably supported by the stationary gantry 104 and rotates around an examination region 108 and a portion of an object or subject therein about a longitudinal or z-axis 110.

A radiation source 112, such as an x-ray tube, is supported by and rotates with the rotating gantry 106 around the examination region 104. The radiation source 112 emits x-ray radiation that is collimated to form a generally fan, wedge, or cone shaped x-ray radiation beam that traverses the examination region 108.

A source controller (SC) 114 controls the radiation source 112. This includes activating the radiation source 112 to emit radiation during time series perfusion imaging to acquire time frame data. Such activation can be temporally continuous or temporally intermittent during an imaging examination for one or more rotations of the radiation source 112, including for the entire or a sub-portion of each rotation of the radiation source 112.

A radiation sensitive detector array 116 subtends an angular arc opposite the radiation source 112 across the examination region 108. The detector array 116 includes one or more rows of detectors that are arranged with respect to each other along the z-axis 110 and detects radiation traversing the examination region 108. The detector array 116 generates projection data (line integrals) indicative of the detected radiation.

A reconstructor 118 reconstructs the projection data generates volumetric image data. For a CTP procedure, this includes reconstructing projection data for sequential acquisitions and generating time series CTP volumetric image data, as described in further detail below. Examples of suitable reconstruction algorithms include filtered backprojection, statistical, iterative, sparse sampling, and/or other reconstruction algorithms.

A subject support 120, such as a couch, supports an object (e.g., a phantom) or subject 122 in the examination region 108. The subject support 120 is movable in coordination with performing an imaging procedure so as to guide the object or subject 122 with respect to the examination region 108 for loading, scanning, and/or unloading the object or subject 122.

An injector 124 is configured to inject or administer a material such as one or more contrast agents to the object or subject 122 to be scanned during a perfusion scan. A contrast agent (e.g., iodine based) can additionally or alternatively be manually administered by a clinician or the like. Where the contrast agent is manually administered to the object or subject 122, the injector 124 can be omitted.

An operator console 126 includes a human readable output device 128 such as a display monitor, a filmer, etc. and an input device 130 such as a keyboard, mouse, etc. The console 124 further includes a processor 132 (e.g., a central processing unit (CPU), a microprocessor, etc.) and computer readable storage medium 134 (which excludes transitory medium) such as physical memory. In the illustrated embodiment, the computer readable storage medium 134 includes a CTP data enhancing module 136. In a variation, the CTP data enhancing module 136 is part of another computing system, which is remote from and not part of the scanner 102.

The illustrated CTP data enhancing module 136 includes computer executable instructions for predicting sequential dense time line CTP volumetric image data from sequential sparse time line CTP volumetric image data generated by the CT scanner 102 (or other scanner) during a CTP imaging scan. As described in greater detail below, the computer executable instructions include a trained neural network to predict the sequential dense time line CTP volumetric image data. In one instance, this allows for performing a temporally intermittent (sparse) CTP scan and producing sequential dense time line CTP volumetric image data, e.g., as if the sequential dense time line CTP volumetric image data were generated from a temporally continuous CTP (dense) imaging scan. As such, patient x-ray dose is decreased (relative to a temporally continuous CTP imaging can) while generating sequential dense time line CTP volumetric image data for accurate CTP parameter measurements.

The computer readable storage medium 134 further includes a CTP data analyzer module 138, which includes computer executable instructions for processing the sequential dense time line CTP volumetric image data produced by the CTP data enhancing module 136 to determine one or more CTP parameters such as a time-attenuation curve, blood flow, blood volume, mean transit time, maximum upslope, time to peak, and/or other perfusion parameter(s). In a variation, the neural network of the CTP data enhancing module 136 is further trained with one or more training CTP parameters generated from the training sequential dense time line CTP volumetric image data to also predict one or more of these CTP parameters from the predicted sequential dense time line CTP volumetric image data. In this variation, the CTP data analyzer module 138 can be omitted.

Figure 2:
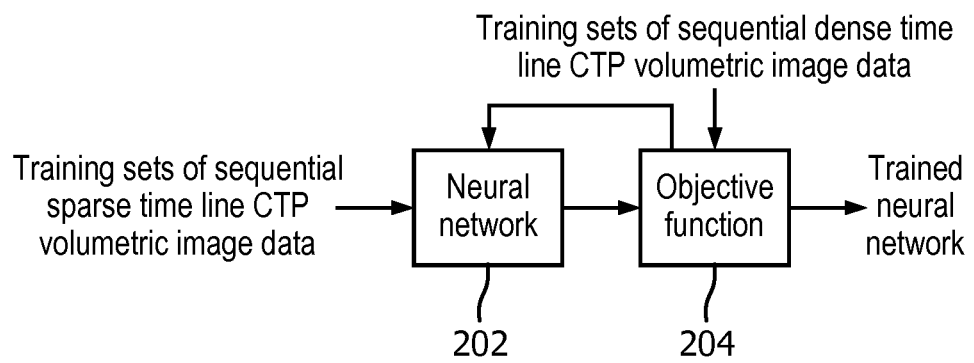
FIG. 2 schematically illustrates an example of training the neural network with sets of training sequential sparse time line CTP volumetric image data and sets of training sequential dense time line CTP volumetric image data.

FIG. 2 schematically illustrates example training of a neural network 202 with training sets of sequential sparse time line CTP volumetric image data and training sets of sequential dense time line CTP volumetric image data. In one instance, the training sparse and dense volumetric image are obtained from a same dense time line CTP scan. For example, the training sets of sequential sparse time line CTP volumetric image data can be derived from the training sets of sequential dense time line CTP volumetric image data, e.g., as a subset thereof (e.g., every other set in time, etc.). Alternatively, the training sparse and dense CTP volumetric image data are obtained through separate CTP imaging scans.

The output of the neural network 202 is evaluated with an objective function 204. In this example, the objective function 204 includes a mathematical function that minimizes an error between the training sets of sequential sparse time line CTP volumetric image data and the training sets of sequential dense time line CTP volumetric image data, e.g., based on a mean squared difference therebetween and/or otherwise. Trainable parameters of the neural network are updated and converge through a number of iterations. In this example, the parameters are updated until the error falls below of predetermined threshold. Other stopping criteria includes a predetermined number of iterations, a predetermined time duration, etc.

In one instance, the objective function 202 is implemented as a cost function L(w), e.g., as shown in EQUATION 1:

$$L(w) = \sum_j \|T(SI; w)_j - DI_j\|_2^2 + \lambda_2 \sum_k \|w_k\|_2^2 \qquad \text{EQUATION 1}$$

where SI is a jth set of training sparse time line CTP volumetric image data, DI is the jth set of training dense time line CTP volumetric image data, and T represents a transformation with trainable parameters w. A regularization term $\lambda_2 \Sigma_j \|w_k\|_2^2$ drives the equation towards small parameters w, $\lambda_2$ represents a hyperparameter, and k represents the layers of neural networks.

Figure 3:
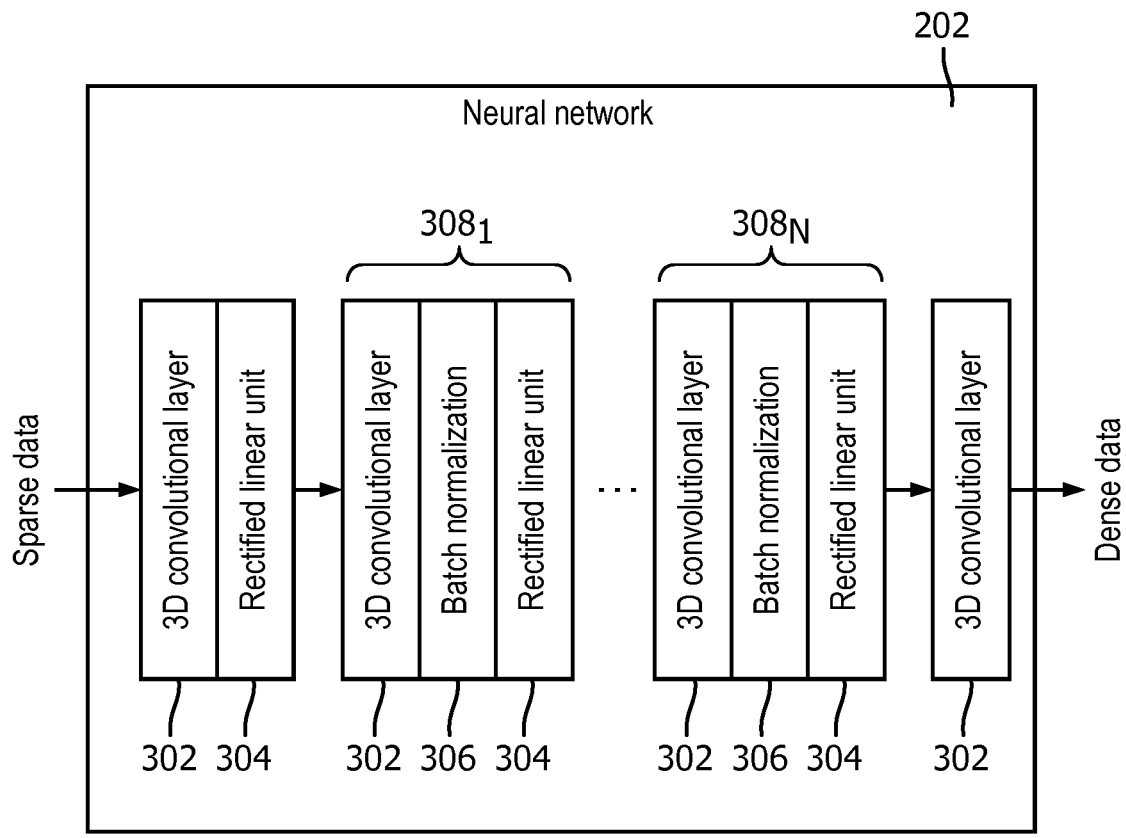
FIG. 3 schematically illustrates an example neural network that can be trained as shown in FIG. 2.

FIG. 3 schematically illustrates an example of a suitable neural network 202 for FIG. 2. The input includes sequential sparse time line CTP volumetric image data (sparse data) and the output includes sequential dense time line CTP volumetric image data (dense data).

In this example, the neural network 202 is a three-dimensional (3-D) convolutional neural network with 3-D convolutional layers 302, rectified linear units 304, and batch normalization 306, with N (where N is an integer equal to or greater than one) sets of 3-D convolutional layer/rectified linear unit/batch normalization middle layers $308_1, \ldots, 308_N$. In one instance, the convolutional kernel used in each convolutional layer is a 3-D kernel. Examples of suitable size kernels includes 3×3×3, 5×5×5, 7×7×7, and/or other size kernels. The number of layers, the kernel size, the number of channels, the learning rate, etc. can be tuned.

In general, each of the convolutional layers includes convolutional neurons that apply a convolution operation to the input. In one instance, this includes convolving a set of kernels across a width and a height of each volume, computing a dot product between the entries of the filter and the volume. Each of the rectified linear units applies a non-linear activation function to its input, which increases nonlinear properties of the overall network. The batch normalization normalizes the output of the 3-D convolutional layers before the output is processed by the rectified linear units. This reduces internal covariate shifts, which can lead to usage of higher learning rates.

Examples of convolution network are further described in Gouk, et al., "Fast Sliding Window Classification with Convolutional Neural Networks," IVNVZ '14 Proceedings of the 29th International Conference on Image and Vision Computing New Zealand, Pages 114-118, Nov. 19-21, 2014, "Fully convolutional networks for semantic segmentation," Proceedings of the IEEE Conference on Computer Vision and Pattern Recognition, 2015, and Ronneberger, et al., "U-Net: Convolution Networks for Biomedical Image Segmentation," Medical Image Computing and Computer-Assisted Intervention (MICCAI), Springer, LNCS, Vol. 9351: 234-241, 2015.

Figure 4:
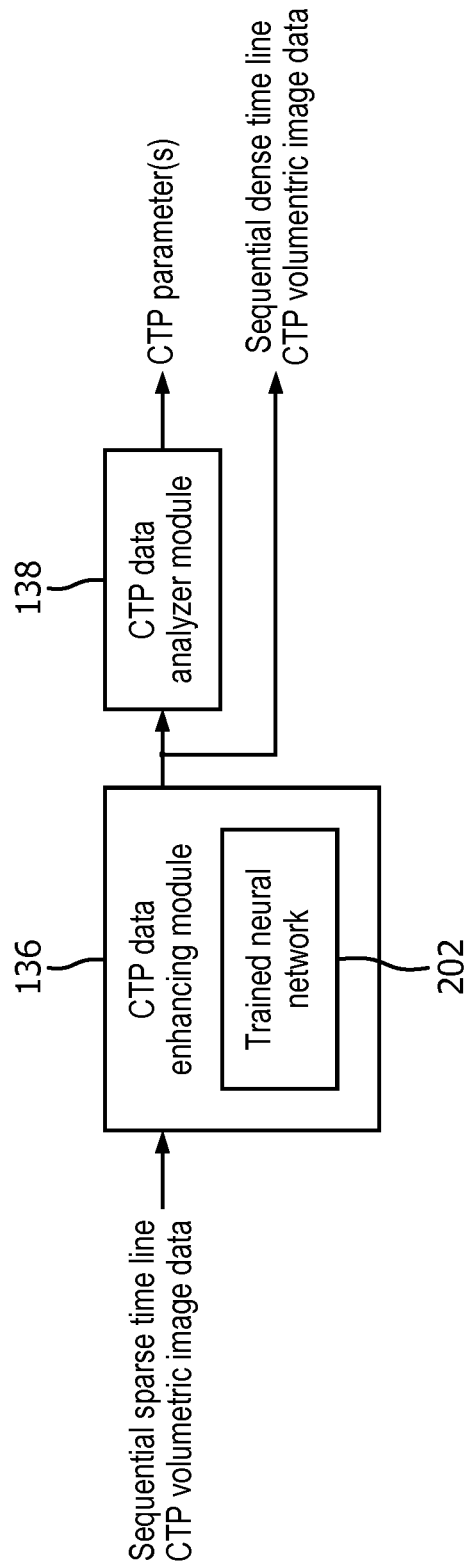
FIG. 4 schematically illustrates the CT scanner employing the neural network of FIG. 3 trained as shown in FIG. 2.

FIG. 4 schematically illustrates an embodiment in which the CTP data enhancing module 136 includes the neural network 202 of FIG. 3 trained in FIG. 2. The trained neural network 202 receives sequential sparse time line CTP volumetric image data generated by the CT scanner 102 (or other scanner) and outputs sequential dense time line CTP volumetric image data. The CTP data analyzer module 138 processes this output and generates one or more CTP parameters such as a time-attenuation curve, blood flow, blood volume, mean transit time, maximum upslope, time to peak, and/or other perfusion parameter(s).

Figure 5:
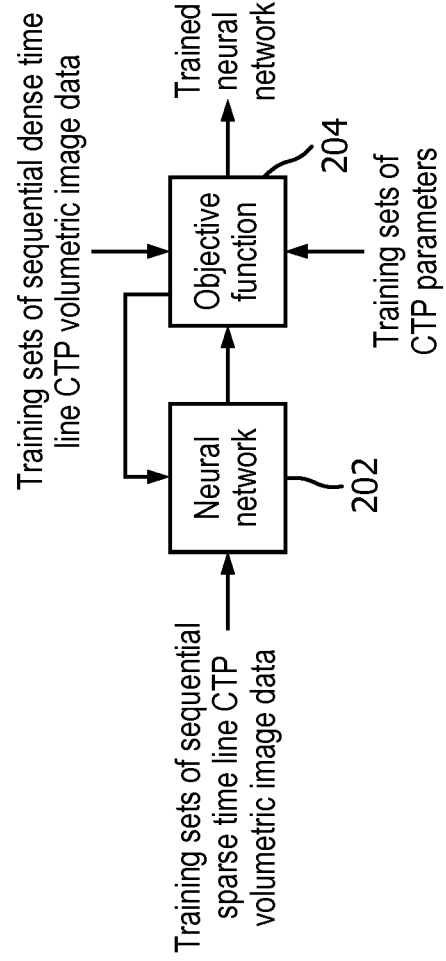
FIG. 5 schematically illustrates an example of further training the neural network with sets of CTP parameters generated with the sets of training sequential dense time line CTP volumetric image data.

FIG. 5 schematically illustrates a variation of FIG. 2 in which the neural network 202 is further trained with training perfusion parameters generated from the training sequential dense time line CTP volumetric image data. In this instance, the objective function 204 is implemented as a cost function L(w,w1) such as the cost function shown in EQUATION 2:

$$L(w, w1) = \sum_j \|T(SI; w)_j - DI_j\|_2^2 + \\ \|TI(SI; w, w1)_j - Bfm_j\|_2^2 + \lambda_2 \sum_k \|w_k\|_2^2 + \|w_{1k}\|_2^2, \qquad \text{EQUATION 2}$$

where TI represents a transformation with the trainable parameters w and perfusion parameter NN trainable parameters w1 and Bfm represents training perfusion parameters generated from the dense time line CTP volumetric image data. In this example, the neural network 202 is trained to predict dense time line CTP volumetric image data as close as possible to true dense time line CTP volumetric image data concurrently with perfusion parameters as close as possible to the true perfusion parameters computed from true dense time line CTP volumetric image data.

Figure 6:
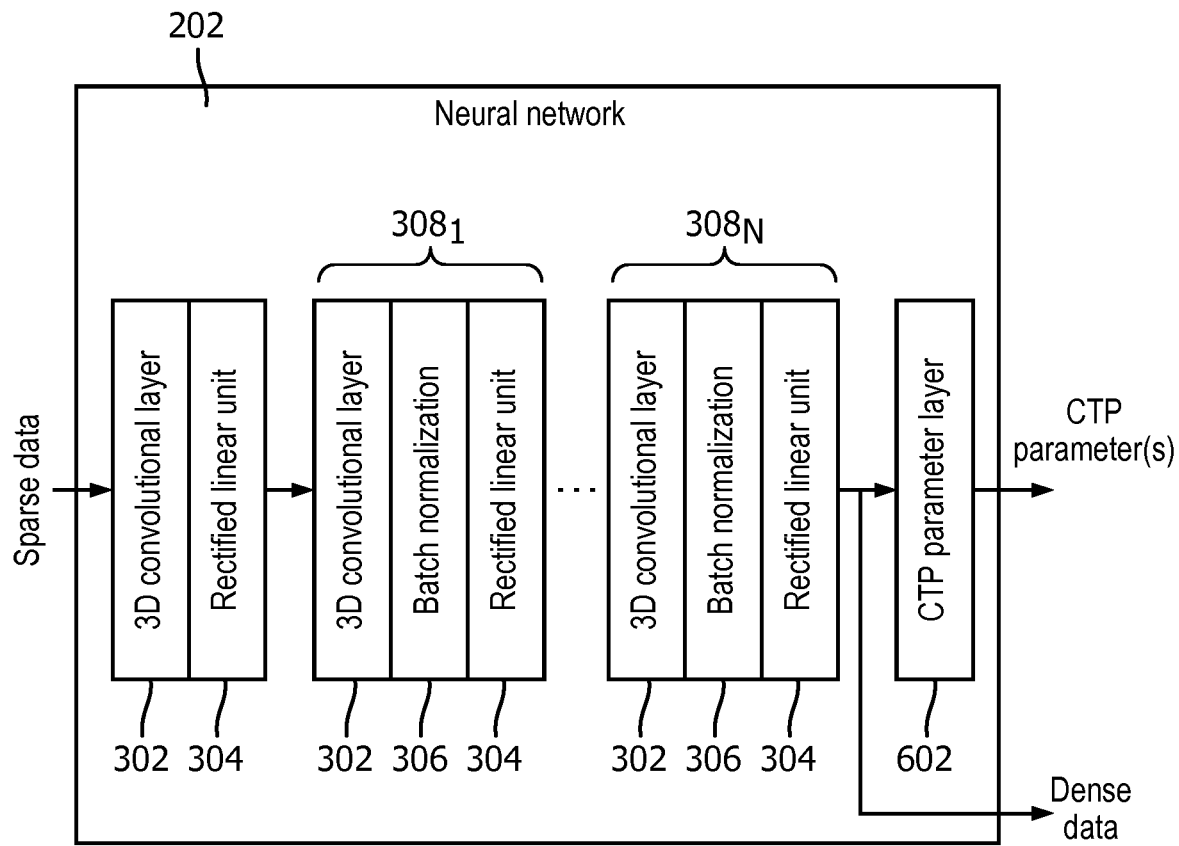
FIG. 6 schematically illustrates an example neural network that can be trained as shown in FIG. 5.

FIG. 6 schematically illustrates an example of a suitable neural network for the neural network 202 of the configuration shown in FIG. 5. In this example, the neural network 202 further includes a CTP parameter layer 602. The CTP parameter concurrently 602 receives the output sequential dense time line CTP volumetric image data and generates one or more CTP parameters therefrom.

Figure 7:
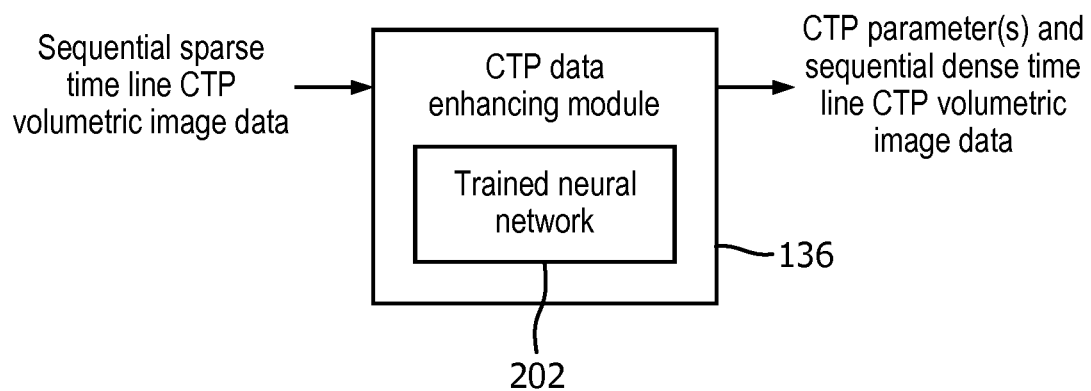
FIG. 7 schematically illustrates the CT scanner employing the neural network of FIG. 6 trained as shown in FIG. 5.

FIG. 7 schematically illustrates an embodiment in which the CTP data enhancing module 136 includes the neural network 202 of FIG. 6 trained in FIG. 5. The trained neural network 202 receives sequential sparse time line CTP volumetric image data generated by the CT scanner 102 (or other scanner) and outputs both sequential dense time line CTP volumetric image data and one or more CTP parameters.

Figure 8:
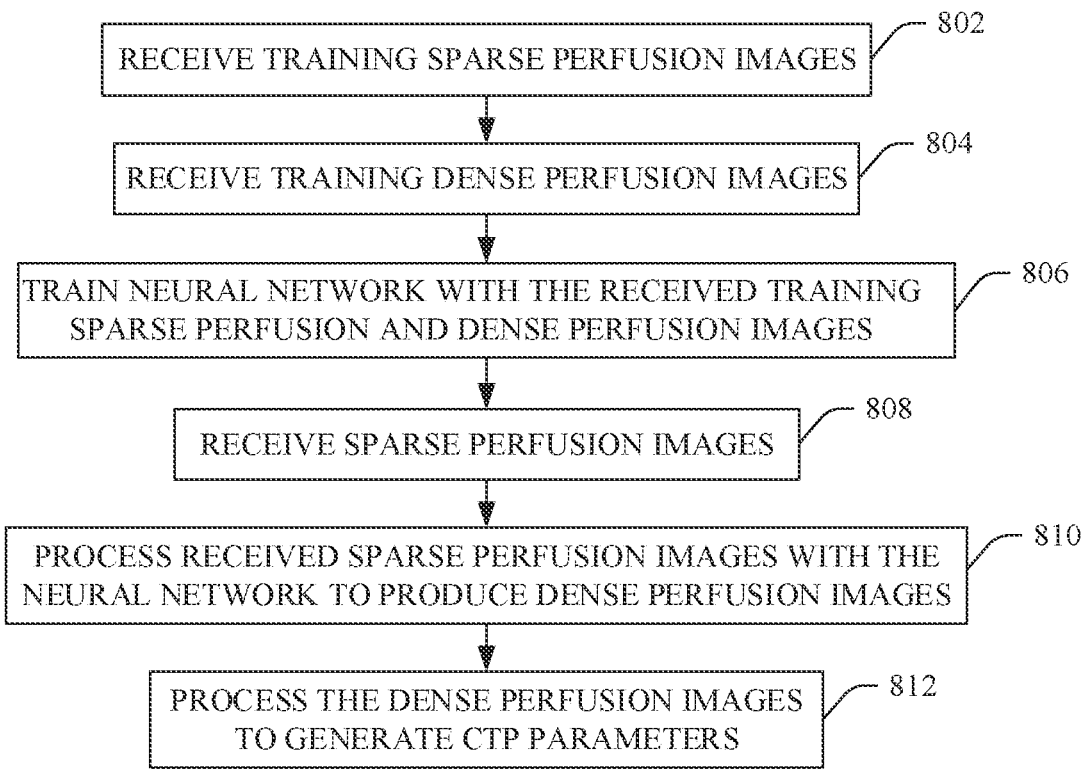
FIG. 8 illustrates an example method in accordance with an embodiment herein.

FIG. 8 illustrates an example method in accordance with the embodiment described in FIGS. 2-4.

It is to be appreciated that the ordering of the acts in the method is not limiting. As such, other orderings are contemplated herein. In addition, one or more acts may be omitted, and/or one or more additional acts may be included.

At 802, a set of training sparse perfusion images is received, as described herein and/or otherwise.

At 804, a set of training dense perfusion images is received, as described herein and/or otherwise.

At 806, the set of training sparse perfusion images and the set of training dense perfusion images are employed to train a neural network, as described herein and/or otherwise.

At 808, sparse perfusion images are received, as described herein and/or otherwise.

At 810, the sparse perfusion images are processed with the trained neural network to produce dense perfusion images.

At 812, the dense perfusion images are processed to generate CTP parameters.

Figure 9:
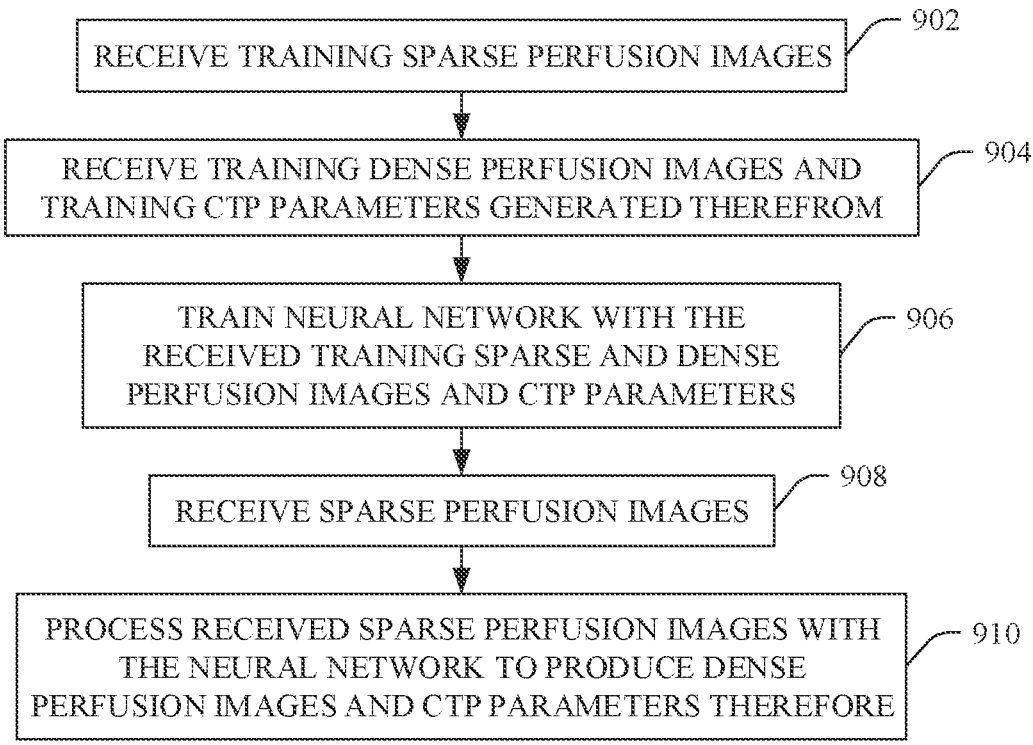
FIG. 9 illustrates another example method in accordance with an embodiment herein.

FIG. 9 illustrates an example method in accordance with an embodiment described in FIGS. 5-7.

It is to be appreciated that the ordering of the acts in the method is not limiting. As such, other orderings are contemplated herein. In addition, one or more acts may be omitted, and/or one or more additional acts may be included.

At 902, a set of training sparse perfusion images is received, as described herein and/or otherwise.

At 904, a set of training dense perfusion images and a set of CTP parameters generated therefrom are received, as described herein and/or otherwise.

At 906, the set of training sparse perfusion images, the set of training dense perfusion images, and the set of CTP parameters are employed to train a neural network, as described herein and/or otherwise.

At 908, sparse perfusion images are received, as described herein and/or otherwise.

At 910, the sparse perfusion images are processed with the trained neural network to produce dense perfusion images and CTP parameters therefrom.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a -state medium supplied together with or as part of other hardware, but may also be distributed in other forms, such as via the Internet or other wired or wireless telecommunication systems. Any reference signs in the claims should not be construed as limiting the scope.

The invention claimed is:

1. A computed tomography scanner, comprising:
a radiation source configured to emit x-ray radiation;
a detector array configured to detect the x-ray radiation and generate a signal indicative thereof;
a reconstructor configured to reconstruct the signal and generate sequential sparse time line perfusion volumetric image data; and
a processor configured to process the sequential sparse time line perfusion volumetric image data using a trained neural network to produce sequential dense time line perfusion volumetric image data, wherein the processor trains the neural network with 1) training sets of sequential sparse time line perfusion volumetric image data, 2) training sets of sequential dense time line perfusion volumetric image data, and 3) training sets of perfusion parameters generated from the training sets of sequential dense time line perfusion volumetric image data.

2. The scanner of claim 1, wherein the processor is further configured to process the sequential dense time line perfusion volumetric image data to produce one or more perfusion parameters.

3. The scanner of claim 2, wherein the processor employs the trained neural network to produce both the sequential dense time line perfusion volumetric image data and the one or more perfusion parameters.

4. The scanner of claim 2, wherein the processor employs a different neural network to produce the one or more perfusion parameters.

5. The scanner of claim 2, wherein the processor is further configured to produce the one or more perfusion parameters.

6. The scanner of claim 1, wherein the training sets of sequential sparse time line perfusion volumetric image data are sub-sets of the training sets of sequential dense time line perfusion volumetric image data.

7. A computed tomography scanner, comprising:
a radiation source configured to emit x-ray radiation;
a detector array configured to detect the x-ray radiation and generate a signal indicative thereof;
a reconstructor configured to reconstruct the signal and generate sequential sparse time line perfusion volumetric image data; and
a processor configured to train a neural network to predict sequential dense time line perfusion volumetric image data from 1) training sequential sparse time line perfusion volumetric image data, 2) training sequential dense time line perfusion volumetric image data, and 3) training sets of perfusion parameters generated from the training sets of sequential dense time line perfusion volumetric image data.

8. The scanner of claim 7, wherein the training sets of sequential sparse time line perfusion volumetric image data are sub-sets of the training sets of sequential dense time line perfusion volumetric image data.

9. The scanner of claim 7, wherein the processor trains the neural network until an output of a cost function minimizes a difference between the generated sets of sequential dense time line perfusion volumetric image data and the training sets of sequential dense time line perfusion volumetric image data.

10. The scanner of claim 7, where the processor is configured to process the sequential sparse time line perfusion volumetric image data with the trained neural network to produce sequential dense time line perfusion volumetric image data.

11. The scanner of claim 10, wherein the processor is further configured to process the sequential dense time line perfusion volumetric image data to produce one or more perfusion parameters.

12. The scanner of claim 7, where the processor is configured to process the sequential sparse time line perfusion volumetric image data with the trained neural network to produce sequential dense time line perfusion volumetric image data and one or more perfusion parameters.

13. A non-transitory computer readable storage medium encoded with computer readable instructions, which, when executed by a processor of a computing system, cause the processor to:
process sequential sparse time line perfusion volumetric image data using a trained neural network to produce sequential dense time line perfusion volumetric image data, wherein the neural network is trained with 1) training sets of sequential sparse time line perfusion volumetric image data, 2) training sets of sequential dense time line perfusion volumetric image data, and 3)

training sets of perfusion parameters generated from the training sets of sequential dense time line perfusion volumetric image data.

14. The non-transitory computer readable storage medium of claim 13, wherein executing the computer readable instructions further causes the processor to:
process the sequential dense time line perfusion volumetric image to produce one or more perfusion parameters.

* * * * *